United States Patent [19]

Philpot, Jr.

[11] 3,999,538
[45] Dec. 28, 1976

[54] METHOD OF BLOOD VISCOSITY DETERMINATION

[76] Inventor: Van B. Philpot, Jr., P.O. Box 312, Houston, Miss. 38851

[22] Filed: May 22, 1975

[21] Appl. No.: 579,871

[52] U.S. Cl. .............................. 128/2 G; 128/2 F; 73/393
[51] Int. Cl.$^2$ ......................................... A61B 5/02
[58] Field of Search ............. 128/2 F, 2 G, 2.05 D, 128/2.05 E, 2.05 F, 2.05 R; 73/55, 327, 387, 393, 398

[56] References Cited

UNITED STATES PATENTS

| | | | |
|---|---|---|---|
| 3,730,168 | 5/1973 | McWhorter | 128/2 F |
| 3,785,772 | 1/1974 | Coggeswall | 128/2 G |
| 3,834,372 | 9/1974 | Turney | 128/2 F |

Primary Examiner—Anton O. Oechsle
Assistant Examiner—Marvin Siskind
Attorney, Agent, or Firm—Cushman, Darby & Cushman

[57] ABSTRACT

A method of determining blood viscosity of blood in the body. Venous pressure in a body vein is maintained at a constant pressure. Blood is then withdrawn from the vein at a constant pressure for a time period and the volume of blood withdrawn is determined, to obtain an indication of blood viscosity when in the body. The time period can be constant and the blood volume is then proportional to body blood viscosity. Alternately a predetermined volume of blood is withdrawn and the time period is measured and is proportional to blood viscosity in the body. Preferably a three-way valve is incorporated into a system comprising a needle, syringe and vacuum gauge to enable withdrawal of blood at a predetermined negative pressure so that blood viscosity can be obtained rapidly and inexpensively.

22 Claims, 2 Drawing Figures

METHOD OF BLOOD VISCOSITY DETERMINATION

BACKGROUND OF THE INVENTION

It has now been found that the in vivo viscosity of blood varies among individuals and that a substantially in vivo viscosity measurement of blood corresponding to the viscosity when the body can be of value to the physicians in the diagnosis of certain body conditions. The present invention provides means and methods for rapidly and inexpensively determining comparative substantially in vivo blood viscosity. The measurement of blood viscosity long after removal from the patient has been carried out in the past. However, viscosity on whole blood has not been studied thoroughly because of the difficulties in the settling of erythrocytes and of the very dramatic changes that occur in blood following its withdrawal from the cardiovascular system.

SUMMARY OF THE INVENTION

It is an important object of this invention to provide methods for determining in vivo blood viscosity rapidly and in an uncomplicated fashion.

Another object of this invention is to provide methods in accordance with the preceding object which can be carried out with simplified equipment without the need for highly trained personnel yet accurately indicates in vivo blood viscosity.

Still another object of this invention is to provide apparatus for carrying out the methods of the preceding objects.

According to the invention, in vivo blood viscosity is determined by first determining venous pressure in a body vein. Blood is then withdrawn from the vein at a constant pressure for a predetermined time period with the volume of blood withdrawn acting as an indiction of blood viscosity in the body.

In the preferred embodiment, venous pressure is maintained at a constant value with the aid of a blood pressure cuff set for example at 30 mm of mercury. Vena puncture is then made below the blood pressure cuff so that venous pressure remains constant. The vena puncture is preferably carried out by a needle interconnected with a three-way stopcock, one passageway of which leads to a vacuum gauge and the other passage of which leads to a standard Luer syringe. By monitoring the vacuum gauge while retracting the plunger, constant negative pressure can be maintained in the syringe for a predetermined period as for example 15 seconds. At the end of 15 seconds, the volume of blood withdrawn is measured. The variation in volume of blood is found to correspond to and be proportional to blood viscosity of the blood in the body.

In an alternate method of this invention, the syringe plunger is retracted to a predetermined extracted blood volume under a constant negative pressure and the time period necessary to withdraw that volume of blood is measured. That time period is proportional to the viscosity of the blood within the body.

Preferably a device for predetermining blood viscosity rapidly and inexpensively with uncomplicated equipment, comprises a three passage valve, a blood collecting body connected to one passage, a pressure monitoring device connected to a second passage and a needle connected to a third passage. Means for creating a vacuum in the blood collecting body enables one to draw blood into the body under a predetermined negative pressure monitored by the pressure monitoring device.

It is an advantage of this invention that the apparatus needed can be extremely inexpensive and the test can be carried out rapidly without the need for highly trained medical personnel. Tests of this type can easily be carried out by technicians such as medical laboratory technicians without medical doctor supervision. The results obtained can be compared with standardized charts of for example volumes withdrawn in predetermined time periods under similar conditions with different classes of persons such as persons who have myocardial infractions, healthy males, healthy females, men and women of predetermined ages and the like.

BRIEF DESCRIPTION OF THE DRAWINGS

The above and other features will be better understood from a reading of the following specification in connection with the accompanying drawing in which.

DESCRIPTION OF PREFERRED EMBODIMENTS

Figure 1:
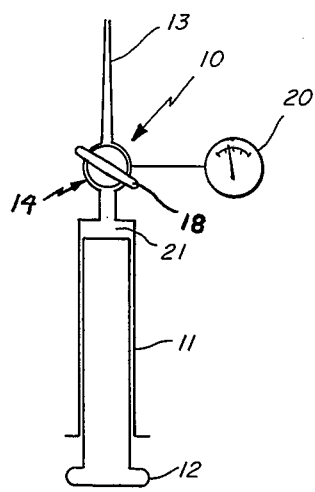
FIG. 1 is a semidiagrammatic showing of an apparatus in accordance with a preferred embodiment of this invention.
Figure 2:
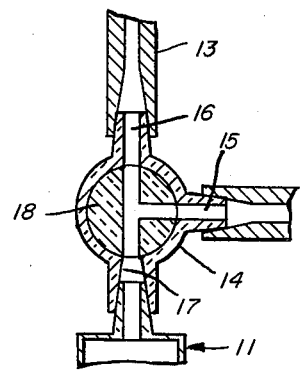
FIG. 2 is a cross sectional view through a stopcock member thereof.

With reference now to the drawings and more particularly FIG. 1, an apparatus for determining blood viscosity is shown at 10. The apparatus comprises a substantially conventional syringe 11 having a plunger 12. The syringe can have a size of from 1 to 50 cc or larger. A conventional 20 gauge needle 13 is locked to a three-way stopcock 14 having a first passageway 16. A second passageway 15 is connected with a third passageway 17 leading to the syringe blood collecting body portion 21. Passageway 15 interconnects a conventional vacuum gauge 20 with the three passageways. A shuttle 18 enables blocking of all three passageways and selective interconnection of all three passageways when desired.

In a typical example of carrying out the method of this invention, a conventional blood pressure cuff of a blood pressure manometer is applied to the arm about 2 inches above the subcubital arm vein of a human test subject. Thirty millimeters of mercury are maintained in an inflated blood pressure cuff. A vena puncture is performed below the cuff using the needle 13 which is a 1½ inch 20 gauge needle. The shuttle handle 18 allows all three passageways to be opened. The plunger 12 is withdrawn for a time of 15 seconds while monitoring the vacuum with the manometer or vacuum gauge 20 to maintain it at 3–10 inches of mercury and preferably 6 inches of mercury. The volume of blood removed is then measured by the calibrations in the syringe. This volume is indicative and proportional to blood viscosity in vivo in the body from which the blood has been withdrawn. If the blood is thinner than a set standard, a greater volume will be withdrawn in the predetermined constant time period than if it is thicker than a set standard.

It has been found that the blood viscosity of different groups of human subjects varies greatly. Thus a comparative measurement at predetermined conditions on a large group of individuals can enable useful diagnostic information to be obtained on a single sample by comparison of that sample with charts previously made under similar conditions.

The values of the table below were obtained using the method of the above example. As seen in the table, a total of 6 volunteer normal females were used, and the average amount of blood withdrawn was 8.9 cc. A total of 8 adult males were used and the average amount of blood was 7.2 cc. After exercise, the amount of blood withdrawn from one of the male volunteers increased from 7.0 to 7.4 and in a second volunteer male, the amount of blood withdrawn after exercise increased from 7.0 to 8.0.

Results of this particular test from patients with myocardial infarction shows a significant decrease in the amount of blood withdrawn by this method. The average amount of blood drawn from 2 females with myocardial infarction was 7.0 in contrast to a normal level of 8.9. The average of 2 male patients with myocardial infarction was 4.1 in contrast to a normal average in males of 7.2.

AMOUNT OF BLOOD DRAWN FROM VENIPUNCTURE
AT 6 IN. VACUUM FOR 15 SECONDS

| Normal Volunteers Basal Conditions | | Normal Volunteers After Exercise | Patients with Myocardial Infarct | |
|---|---|---|---|---|
| Female | Male | Male | Female | Male |
| 9.10 | 7.0 |  | 6.2 | 4.6 |
| 8.90 | 8.0 |  | 7.8 | 3.5 |
| 9.00 | 7.0 | 7.4 |  |  |
| 8.90 | 7.3 |  |  |  |
| 8.80 | 7.0 | 8.0 |  |  |
| 8.90 | 7.5 |  |  |  |
|  | 7.1 |  |  |  |
|  | 7.1 |  |  |  |
| Average: |  |  |  |  |
| 8.9 | 7.2 | 7.7 | 7 | 4.1 |
| 53.60 = 8:93 |  | 58:00 = 7:25 | 14: = 7 | 8:10 = 4:05 |

In a modification of this invention, the method is duplicated except that the syringe is withdrawn to a predetermined volume as for example 30 cc and the time of withdrawl of blood is measured rather than being set at a constant. The variation in time to remove a predetermined constant volume of blood is then the variable which is proportional to blood viscosity. Similar charts can be obtained based on time variations rather than volume variations if desired. It has been found that volume variations provide a simpler and more effective means of determining blood viscosity on a comparative basis than time variations.

While a three-way valve is preferred for usage in the present invention, various apparatus modifications may be made within the scope of this invention. In some cases, the manometer or other pressure gauge measurement can be incorporated directly in the blood collecting body rather than being attached through a three-way valve. In some cases it may be desirable to provide a water jacket surrounding the syringe to maintain a constant temperature about the blood collecting chamber. This would provide some greater degree of accuracy although at ambient temperatures normally encountered, the blood remains substantially at body temperature throughout the viscosity measurement in accordance with this invention. Thus temperature variations are of little significance.

In all cases, it is preferred to maintain a constant venous pressure during withdrawal and measurement of the blood, and to subject the blood to a constant negative pressure to aid withdrawal. Preferably the venous pressure applied by the cuff is in the range of from 10 mm to 70 mm, the negative pressure applied by the plunger is in the range of from 1 inch to 20 inches, and the time of withdrawal is in the range of from 5 seconds to 60 seconds. Preferably predetermined charts are set up for comparison of blood volumes withdrawn in predetermined time constant periods, at predetermined constant negative pressure through predetermined constant needle sizes at substantially ambient temperatures preferably in the range of from 65° to 80° F. Alternately the charts are based on comparisons of time of withdrawal with constant volumes withdrawn. The viscosity measurement is made within seconds of withdrawal of blood from the body thus avoiding viscosity changes due to settling of blood components as well as other dramatic physical and chemical changes which occur in blood with the passage of time after removal from the body.

I claim:
1. A method of determining in vivo blood viscosity, said method comprising,
    determining venous pressure in a body vein,
    withdrawing blood from said vein at a constant pressure for a time period and determining the volume of blood withdrawn,
    and obtaining an indication of blood viscosity of said blood when in the body.
2. A method in accordance with the method of claim 1 wherein said time period is maintained at a predetermined constant and said volume of blood withdrawn is a variable, proportional to said blood viscosity.
3. A method in accordance with the method of claim 2 wherein said venous pressure is determined in said body vein by applying external pressure to said vein.
4. A method in accordance with the method of claim 3 wherein said venous pressure is determined by an inflatable cuff applying a predetermined pressure to said vein during said withdrawing step.
5. A method in accordance with the method of claim 4 wherein said blood is withdrawn from said vein by means of a syringe with a plunger utilized to apply a negative pressure in said syringe at a constant value measured by a vacuum gauge during withdrawal for a preselected constant time period.
6. A method in accordance with the method of claim 5 and further comprising obtaining a volume indication and comparing said volume indication with others obtained from body veins of others to thereby afford a comparison with blood viscosity of known individual types and conditions.
7. In a diagnostic method of measuring whole blood viscosity in vivo of a subject animal, the steps comprising:
    1. determining and maintaining a substantially constant venous pressure in a body vein of the subject containing blood;
    2. withdrawing blood from said vein at a point distal from the point of maintaining substantially constant venous pressure;
        a. through an opening of a predetermined effective dimension,
        b. under conditions of a predetermined substantially constant negative pressure so as to establish a corresponding predetermined substantially constant fluid pressure drop across said opening, and
        c. for a predetermined period of time and until a variable volume sample of blood has been withdrawn from said vein;

3. measuring the volume of blood so withdrawn in step (2) which blood volume is inversely proportional to the in vivo viscosity of the whole blood contained in said subject.

8. The diagnostic method of claim 7 wherein the substantially constant venous blood pressure is maintained by applying external pressure to the vein.

9. The diagnostic method of claim 8 wherein the external pressure is applied to the vein by means of an inflatable cuff.

10. The diagnostic method of claim 7 wherein the blood withdrawn in step (2) is removed by and contained in a calibrated syringe.

11. The diagnostic method of claim 7 wherein the venous pressure is maintained at 10–70 mm mercury.

12. The diagnostic method of claim 7 wherein the negative withdrawal pressure of step (2)(b) is 1–20 inches of mercury.

13. The diagnostic method of claim 7 wherein the withdrawal time of step (2)(c) is for a period of 5–60 seconds.

14. The diagnostic method of claim 7 including the further step of: (4) diagnosing from the blood viscosity value determined in step (3) an abnormal body condition of said subject.

15. The diagnostic method of claim 7 including the further step of: (4) diagnosing from the blood viscosity value determined in step (3) an abnormal body condition of said subject.

16. In a diagnostic method of measuring whole blood viscosity in vivo of a subject animal, the steps comprising:
 1. maintaining a substantially constant venous pressure in a body vein of said subject containing blood;
 2. withdrawing blood from said vein at a point distal from the point of maintaining a substantially constant venous pressure;
  a. through an opening of predetermined effective dimension,
  b. under conditions of a predetermined substantially constant negative pressure so as to establish a corresponding predetermined substantially constant fluid pressure drop across said opening, and
  c. for a variable amount of time to withdraw a predetermined volume of blood, from said vein; and
 3. measuring the time required to withdraw the predetermined volume of blood withdrawn under the conditions of step (2) which measured withdrawal time is directly proportional to the in vivo viscosity of the whole blood contained in said subject.

17. The diagnostic method of claim 16 wherein the substantially constant venous blood pressure is maintained by applying external pressure to the vein.

18. The diagnostic method of claim 17 wherein the external pressure is applied to the vein by means of an inflatable cuff.

19. The diagnostic method of claim 16 wherein the blood withdrawn in step (2) is removed by and contained in a calibrated syringe.

20. The diagnostic method of claim 16 wherein the venous pressure is maintained at 10–70 mm mercury.

21. The diagnostic method of claim 16 wherein the negative withdrawal pressure of step (2) (b) is 1–20 inches of mercury.

22. A method of determining in vivo blood viscosity, said method comprising,
 determining venous pressure in a body vein,
 withdrawing a predetermined volume of blood from said vein at a constant pressure and determining the time required to withdraw said predetermined volume, wherein the time period is proportional to said blood viscosity,
 and obtaining an indication of blood viscosity of said blood when in the body.

* * * * *

REEXAMINATION CERTIFICATE (226th)
United States Patent [19]
Philpot, Jr.

[11] B1 3,999,538

[45] Certificate Issued Jul. 24, 1984

[54] METHOD OF BLOOD VISCOSITY DETERMINATION

[76] Inventor: Van B. Philpot, Jr., P.O. Box 312, Houston, Miss. 38851

Reexamination Request:
No. 90/000,349, Mar. 30, 1983

Reexamination Certificate for:
Patent No.: 3,999,538
Issued: Dec. 28, 1976
Appl. No.: 579,871
Filed: May 22, 1975

[51] Int. Cl.$^3$ .............................................. A61B 5/02
[52] U.S. Cl. .................................................... 128/637
[58] Field of Search ......................................... 128/637

[56] References Cited
PUBLICATIONS

Pringle et al., "Blood Viscosity and Raynaud's Disease", *The Lancet*, pp. 1086–1088, May 22, 1965.

*Primary Examiner*—Lee S. Cohen

[57] ABSTRACT

A method of determining blood viscosity of blood in the body. Venous pressure in a body vein is maintained at a constant pressure. Blood is then withdrawn from the vein at a constant pressure for a time period and the volume of blood withdrawn is determined, to obtain an indication of blood viscosity when in the body. The time period can be constant and the blood volume is then proportional to body blood viscosity. Alternately a predetermined volume of blood is withdrawn and the time period is measured and is proportional to blood viscosity in the body. Preferably a three-way valve is incorporated into a system comprising a needle, syringe and vacuum gauge to enable withdrawal of blood at a predetermined negative pressure so that blood viscosity can be obtained rapidly and inexpensively.

REEXAMINATION CERTIFICATE ISSUED UNDER 35 U.S.C. 307.

THE PATENT IS HEREBY AMENDED AS INDICATED BELOW.

AS A RESULT OF REEXAMINATION, IT HAS BEEN DETERMINED THAT:

Claims 1-22 are cancelled.

* * * * *